United States Patent [19]

Brackenridge et al.

[11] 4,171,456

[45] Oct. 16, 1979

[54] α,α'-BIS(2-HYDROXYETHOXY)-2,3,5,6-TETRABROMO-P-XYLENE

[75] Inventors: David R. Brackenridge, Royal Oak, Mich.; Lawrence C. Mitchell, Mt. Vernon, Ind.

[73] Assignee: Ethyl Corporation, Richmond, Va.

[21] Appl. No.: 838,725

[22] Filed: Oct. 3, 1977

Related U.S. Application Data

[63] Continuation-in-part of Ser. No. 571,787, Apr. 25, 1975, abandoned.

[51] Int. Cl.$^2$ .............................................. C07C 43/28
[52] U.S. Cl. .............................. 568/663; 260/45.85 R; 528/425; 528/397
[58] Field of Search ..................... 260/611 A; 568/663

[56] References Cited

U.S. PATENT DOCUMENTS

| | | | |
|---|---|---|---|
| 2,799,694 | 6/1957 | Ross et al. | 260/611 A X |
| 3,068,294 | 12/1962 | Rosen et al. | 260/611 A |
| 3,956,399 | 5/1976 | Paritee et al. | 260/613 R X |
| 4,002,688 | 1/1977 | Loeb et al. | 260/613 R |

OTHER PUBLICATIONS

Slezak et al., Ind. Eng. Chem. Prod. Res., Develop 4, (1965), pp. 259–261.

*Primary Examiner*—Bernard Helfin
*Attorney, Agent, or Firm*—Donald L. Johnson; John F. Sieberth; Robert A. Linn

[57] ABSTRACT

The title compound can be made by reacting ethylene glycol with hexabromo-p-xylene in the presence of anhydrous potassium carbonate. The compound is useful as a fire retardant for plastics, and can be used to form a polyester of the linear type. Fibers made from such polyesters are useful for making fire retardant textiles, carpets, drapes, and garments.

1 Claim, No Drawings

α,α'-BIS(2-HYDROXYETHOXY)-2,3,5,6-TETRABROMO-P-XYLENE

REFERENCE TO RELATED APPLICATION

This application is a continuation-in-part of application Ser. No. 571,787 filed Apr. 25, 1975 and now abandoned.

BACKGROUND OF THE INVENTION

α,α'-Bis(2-hydroxyethoxy)-2,3,5,6-tetrachloro-p-xylene, and a cross-linked polyester made therefrom is disclosed in Slezak et al, *Ind. Eng. Chem. Prod. Res. Develop.* 4, 259–61 (1965). Related compounds and polyesters are disclosed.

Parent application Ser. No. 571,787 supra teaches a certain by-product was formed during the process of the Example. The by-product was illustrated by formula (III), on page 4 of the parent application. Work conducted after the parent case was filed has indicated that the compound of Formula (III) was not a principal by-product as previously believed. This application appropriately reflects the new knowledge.

SUMMARY OF THE INVENTION (1) α,α'-Bis(2-hydroxyethoxy)-2,3,5,6-tetrabromo-p-xylene that is, the compound having the formula

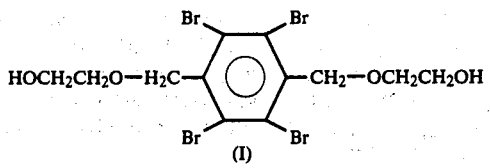

and (2) linear polyester made therefrom wherein about 2 to about 100 mole percent of the diol is compound (I).

Such polyesters can be employed to prepare polyester fiber having improved light stability and/or fire retardancy. Likewise, Compound (I) can be used to prepare fire retardant polyurethanes, and fire retardant cross-linked polyester. The compound is also useful as a chemical intermediate.

DESCRIPTION OF PREFERRED EMBODIMENTS

A preferred way to prepare the compound of Formula (I) is to react hexabromo-p-xylene

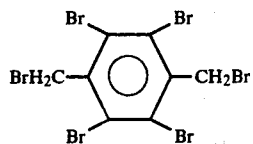

with ethylene glycol under substantially anhydrous conditions, and in the presence of a base which does not react deleteriously with the reactants or desired product. The alkaline system preferably reacts in a manner such that (1) all or substantially all hydrogen halide by-products becomes bound to the base and (2) the acid-base neutralization which takes place does not result in formation of an appreciable quantity of water. Water can be deleterious since it causes undesirable by-product formation.

Metal carbonates, used in an amount of at least about 2 moles and up to about 5 moles per mole of xylylene dihalide starting material, are preferred basic systems. Preferably, $Na_2CO_3$ or $K_2CO_3$ are used in such molar amounts. There is no real upper limit on the amount of base; this being governed by secondary considerations such as economics.

Slightly elevated temperatures, say within the range of 110°–160° C., can be employed. Reaction times of 0.5–5.0 hours at such temperatures can suffice. The pressure is not critical; elevated pressures can be used if reaction is desired above the normal boiling point of a constitutent in the reaction zone. Reaction is facilitated by using an excess of ethylene glycol; from about 2.5 to about 100 moles of glycol per mole of xylylene dihalide (I) are preferred. There is no real upper limit on the amount of glycol, this too is governed by such secondary considerations as economics, reaction vessel size, degree of fluidity desired, etc.

As stated above, this reaction is conducted under substantially anhydrous conditions. Thus, the process of this invention is conducted in the substantial absence of water. Some water can be tolerated, but it is preferred to have less than about 0.5 and more preferably less than about 0.1 weight percent water in the reaction zone.

The mechanism for the marked, unexpected beneficial effect of the use of at least two moles of metal carbonate per mole of xylylene halide starting material is not fully understood. It is believed that the beneficial effect is obtained by decreasing the amount of water in the reaction system. Apparently water can compete with the glycol for reaction with hexabromo-p-xylene; one reaction with water which can lead to extraneous product formation is depicted as follows:

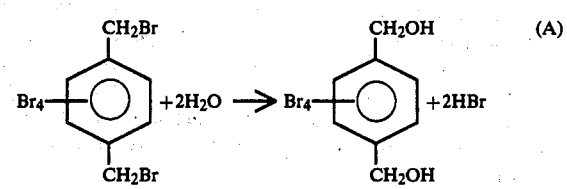

Water can be formed during the course of the reaction when the xylylene dibromide and alkali metal carbonate are reacted in equimolar amounts as shown by the following equation:

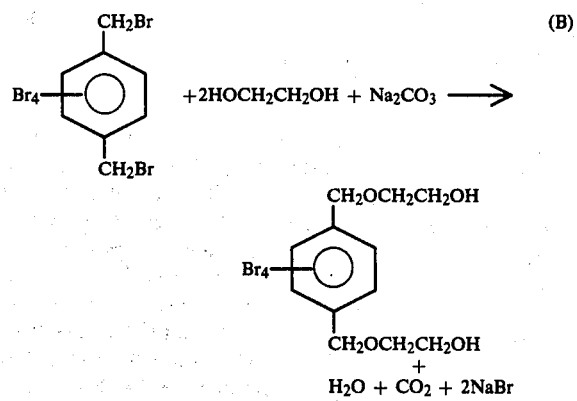

Without being bound by any theory, it is believed the beneficial effect of two moles of metal carbonate can be depicted by the following reaction:

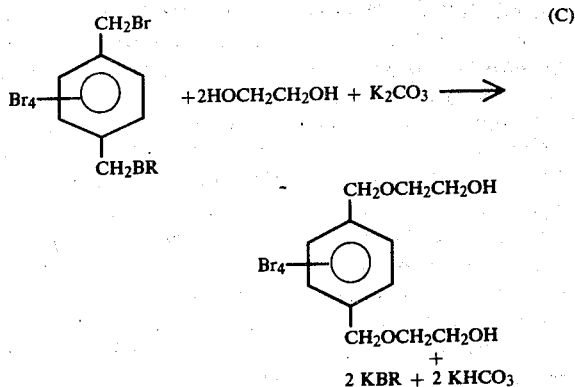

Although not depicted above, it is appreciated by a skilled practitioner that reaction of 2 moles of a glycol with one mole of a xylylene dibromide results in the formation of two moles of HBr. Both of these can combine by neutralization with one mole of alkali metal carbonate. Neutralization of carbonate by the strong acid in this proportion results in formation of $CO_2$ and water.

However, when the two moles of HBr react by neutralization with two moles of alkali metal carbonate, water is not formed; rather the $CO_2$ and protonic portions of the system become bound as $HCO_3^-$.

For the beneficial results of this invention to be obtained it is not necessary that there be exactly two moles of metal carbonate per mole of xylylene dibromide starting material. Somewhat less metal carbonate can be used, but preferably, at least about two moles are employed per mole of xylylene dibromide, and as stated above, more than 2 moles of carbonate can also be used.

It will be apparent that the nature of the metal carbonate is not critical. Thus, it is the concentration that is important and metal carbonates other than those of the alkali metals can be used, for example, magnesium carbonate.

The process of this invention is useful for the reaction of glycols with xylylene dibromides, that is, compounds which can be represented by the following general formula

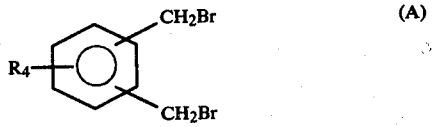

As indicated by the formula, the relative positions of the —$CH_2Br$ groups is not critical; hence, they may be ortho, meta, or para to one another. The radicals appended to the ring and indicated by R in Formula (A) can be selected from a wide variety of radicals which do not interfere with the reaction. Because of their availability, compounds are preferred in which the R radicals are selected from hydrogen and halogen. Of the halogens, bromine is preferred. More preferably, there are at least two bromines and most preferably four attached to the rings.

Reaction of compounds of Formula (A) with glycols under the conditions described herein is illustrated by the following typification which is non-limiting.

EXAMPLE 1

Hexabromo-p-xylene (400 g, 0.69 mole), ethylene glycol (2.5 l, 44.8 mole, reagent grade), and anhydrous potassium carbonate (200 g, 1.2 mole) were charged into a 5 liter, three-necked flask, which was equipped with a mechanical stirrer, and a condenser fitted with a Drierite drying tube. The mixture was heated with stirring to 130° to become homogeneous, and was kept at that temperature for one hour. After being cooled to about 50° C., the mixture was poured into 4 liters of ice water, while stirring. The precipitated solid was collected by filtration and washed with water (1 liter).

Another 400 g of hexabromo-p-xylene was reacted in the same manner as above to prepare the second batch.

A combined total of 789 g of crude product from both batches was dissolved in 3.5 liters of hot isopropanol, and the hot solution was filtered through Celite to remove some insoluble impurity. The filtrate was cooled and filtered to obtain 486 g (65 percent) of the product, αα'-bis(2-hydroxyethoxy)-2,3,5,6-tetrabromo-p-xylene, m.p. 145°–146° C. The product (486 g) was recrystallized from hot isopropanol (but with some inadvertent loss of material). After recrystallization, the product had a melting point of 148°–150° C. NMR (DMSO-$d_6$):S 3.52 (s, 4H, —$OCH_2CH_2O$—), 4.51 (broad, 1H, —OH), 4.98 (s, 2H, —$OCH_2$-bromophenyl).

The mother liquor from the first recrystallization was concentrated to about 1 liter and diluted with 1 liter of $H_2O$ to yield 156 grams of a by-product having a melting point of 110°–120° C. Recrystallization from ethyl methyl ketone gave 100 g of the by-product; melting point at 117°–122° C.

The procedure of the above example can be used with any reaction temperature which yields a suitable amount of desired product in a reasonable reaction time. Temperatures can be selected within the range of 100°–180° C. with 110°–160° C. being preferred.

The example procedure can be carried out for a reaction time of 0.5–5.0 hours with from about 2 to about 100 moles of glycol per mole of dibromine (II), with from at least about 2 to about 5 moles of $Na_2CO_3$ or $K_2CO_3$ initially present in the reaction zone and at ambient or elevated pressures.

It is apparent to a skilled practitioner that the method of this example can be readily modified to prepare other compounds. Thus
hexabromo-m-xylene, or
hexabromo-o-xylene
can be reacted with
ethylene glycol,
1,3-propane diol, or
2-butene-1,4-diol,
or other glycols mentioned
below when discussing polyesters,
to prepare brominated diol products such as
(1) α,α'-bis(2-hydroxyethoxy)-2,4,5,6-tetrabromo-m-xylene
(2) α,α'-bis(2-hydroxyethoxy)-3,4,5,6-tetrabromo-o-xylene
(3) α,α'-bis(3-hydroxypropoxy)-2,4,5,6-tetrabromo-m-xylene
(4) α,α'-bis(3-hydroxypropoxy -3,4,5,6-tetrabromo-o-xylene
(5) α,α'-bis(4-hydroxybut-2-enoxy)-2,4,5,6-tetrabromo-m-xylene (6) α,α'-bis(4-hydroxybut-2-enoxy)-3,4,5,6-tetrabromo-o-xylene when the reaction is conducted with from 2–20 moles of glycol per mole of xylylene bromide at 110°–160° C. for 2–5 hours. Using the same reaction conditions, the brominated diols (7) α,α'-bis(3-hydroxypropoxy-2,3,5,6-tetrabromo-p-xylene and
(8) α,α'-bis(4-hydroxybut-2-enoxy)-2,3,5,6-tetrabromo-p-xylene can also be prepared.

EXAMPLE 2

With stirring, ethylene glycol (71 lbs), 2,3,5,6-tetrabromo-p-xylene (10 lbs), and anhydrous potassium carbonate (5 lbs) were charged into a dried, nitrogen-flushed 20-gallon reaction vessel. The mixture was heated at 130° C. for 1 hour under nitrogen and then cooled to 60° C. Water (86 lbs) was then added with agitation. The resultant cold (25°) mixture was filtered. The reaction vessel was rinsed with 1.5 gallons of water and the resultant wash slurry was also filtered. After washing twice with 1.5 gallon portions of fresh water, the filter cake was broken up on trays and dried in an Abbe dryer at 85° C. and 35 mm. for 7 hours. The filtrate was discarded. The product (8.3 lbs) became a sticky mass with caramel color. It was charged to a ten gallon vessel and was refluxed 2 hours with 48 pounds of isopropanol. The cold (25°) mixture was filtered through a ceramic filter. The filtration was slow, and took one day to finish the filtration and washing to get rid of color. The cake was first dried in an Abbe dryer and then in an air-draft oven to give 5.5 lbs (59 percent) of α,α'-bis(2-hydroxyethoxy)-2,3,5,6-tetrabromo-p-xylene, m.p. 145°–147° C. Analysis Calculated for $C_{12}H_{14}Br_4O_4$: C, 26.6; H, 2.60; Br, 59.0; OH, 6.28. Found: C, 26.5; H, 2.52; Br, 59.4; OH, 5.64. Vapor phase chromatographic analysis indicates that the product was 97.5 percent pure and that it contained the corresponding monoethoxylate (2.4 percent) and an impurity which may have been α,α'-dihydroxytetrabromo-p-xylene, 1,1 percent.

The above isopropyl alcohol-filtrate and washings were combined and concentrated by distilling under atmospheric pressure to a volume of 3 liters. Six liters of water was added. The precipitated solid was filtered and oven-dried to give 1.37 lbs of crude co-product, m.p. 105°–118° C. VPC analysis indicates there are two major and two minor components. One major product is the monoethoxylate (50 percent), and the other is α,α'-bis(2-hydroxyethoxy)-2,3,5,6-tetrabromo-p-xylene(30 percent).

A 3.5 lb sample of the 5.5 lbs of product was refluxed for 3.7 hours in 6.5 lbs of isopropanol in the 10 gallon vessel. The hot solution was filtered through a preheated cartridge filter (1μ) to remove some undissolved impurities. The filtration was slow. At the end of the filtration, there was still some undissolved product in the vessel. More (15.5 lbs) isopropanol was needed to dissolve the solid. The precipitated product was collected by filtering through the ceramic filter. The cake was washed with isopropanol and dried in an air-draft oven (175° F.) to obtain 2.8 lbs (80 percent recovery) of α,α'-bis(2-hydroxyethoxy)-2,3,5,6-tetrabromo-p-xylene with a 99.7 percent purity by VPC analysis, m.p. 148°–150° C.

Above reference was made to Slezak et al, *Ind. Eng. Chem. Prod. Res. Develop.* 4, 259–61 (1965) which discloses a method for preparing α,α'-bis(2-hydroxyethoxy)-2,3,5,6-tetrachloro-p-xylene, a chlorine analog of a compound of this invention. As can be seen by inspection of that reference, particularly page 260, α,α'-2,3,5,6-tetrachloro-p-xylene and ethylene glycol can be made to react by heating these substances to reaction temperature. This suggests to a skilled practitioner that a compound of this invention, α,α'-(2-hydroxyethoxy)-2,3,5,6-tetrabromo-p-xylene, can be made in a similar manner. However, the Slezak et al method employs a large excess of ethylene glycol in order to react with by-product HCl, and make ethylene chlorohydrin. In other words, the Slezak et al method uses comparatively expensive ethylene glycol as a hydrogen halide scavenger. It appears a similar untoward utilization of ethylene glycol would occur if the bromine compound of this invention was made in a similar fashion by substituting α,α'-2,3,5,6-tetrabromo-p-xylene for the chlorine analog in the Slezak et al process. Hence, such a method is not preferred.

To provide compounds of this invention the inventors suggested two routes (a) reaction of ethylene glycol with, e.g., α,α'-2,3,5,6-hexabromo-p-xylene using NaOH as the HBr scavenger, and (b) reaction of ethylene oxide with 2,3,5,6-tetrabromo-p-xylene-α,α' diol. With regard to reaction (a) it would generally proceed as the process or the examples except one would suspect the problems associated with the water formed during the cause of the reaction; for example the water could lead to extraneous by-product formation via reaction (a) supra. Thus, this method is not preferred.

Method (b) likewise is not preferred over that in the Examples. Here there is an inherent problem which can cause extraneous side reactions with loss in yield. Particularly, although some product would be formed, the reaction is difficult to stop with only one —CH$_2$—CH$_2$—OH group added to the starting benzyl nucleus since there is a tendency for additional ethylene oxide to react the newly formed terminal-OH to grow an oligomer or polymeric chain. This problem is aggravated by the difunctional nature of the BrCH$_2$—C$_6$Br$_4$—CH$_2$Br starting material used in the synthesis.

As stated above, the brominated diol, α,α'-bis(2-hydroxyethoxy)-2,3,5,6-tetrabromo-p-xylene can be used as a fire retardant. Compounds (1) through (8) have the same utilities as Compound (I) mentioned above or described below; more specifically, they are useful chemical intermediates and useful for preparing flame retardant cross-linked or linear polyesters, and polyurethanes. With regard to use as an intermediate, they can be esterified with a monobasic acid such as acetic acid to prepare fire retardant additives for polyethylene, polystyrene, and the like.

Likewise, α,α'-dibromo-2,5-dibromo-p-xylene can be reacted with ethylene glycol, 1,3-propanediol, and 2-butene-1,4-diol under reaction conditions similar to those described above to form respectively (9) α,α'-bis(2-hydroxyethoxy)-2,5-dibromo-p-xylene
(10) α,α'-bis(3-hydroxypropoxy)-2,5-dibromo-p-xylene
(11) α,α'-bis(4-hydroxybut-2-enoxy)-2,5-dibromo-p-xylene.

In a similar manner, the other glycols will react to form the expected products. They as well as compounds (9)–(11) are also useful as chemical intermediates and for preparation of polyurethanes, and linear and cross-linked polyesters. Esters such as the acetates of these compounds are also useful as fire retardants for polyethylene, polystyrene and the like. Preferably, the compounds are used to make linear polyesters that are flame retardant, more preferably linear polyester fibers, textiles, and garments which are flame retardant.

Linear polyesters of this invention can be prepared using conventional polymerization procedures. Reaction conditions and catalysts employed can be selected from those described in the art. Thus, typical fiber-forming polyesters of this invention can be made according to the techniques described in the *Encyclopedia of Polymer Science and Technology*, Interscience Publishers, New York, New York (1969), Vol. 11, pages 1–41.

For such linear polyesters, all of the diol content can be selected from one or more of the brominated diols mentioned above. On the other hand, the polyesters may also be made by procedures in which such brominated diol is mixed with one or more glycols conventionally employed in the art. Preferably, from about two to about 100 mole percent of the diol content is a brominated diol of this invention such as Compound I or (1)–(8) described above.

Thus, the brominated diols may be employed as reactive intermediates in the preparation of polyesters obtained from the reaction of glycols of the general formula

wherein x is an integer from about 2 to 10. Such glycols include ethylene glycol, which is a preferred glycol, 1,3-propanediol, 1,5-pentanediol, 1,6-hexanediol, 1,7-heptanediol, 1,8-octanediol, 1,9-nonanediol, 1,10-decanediol, 2,2-dimethyl-1,3-propanediol, 2,2-bis(bromomethyl)-1,3-propanediol or the like. These glycols, and particularly the preferred glycols, ethylene glycol and 1,4-cyclohexane dimethanol, are reacted with dicarboxylic acids or suitable esters thereof, preferably terephthalic acid or dimethyl terephthalate, or other dibasic acids including 2,5-dibromoterephthalic acid, isophthalic acid, diphenyl-4,4'-dicarboxylic acid, naphthalene-2,5-dicarboxylic acid, adipic acid, sebacic acid, succinic acid, oxalic acid, glutaric acid, pimelic acid, suberic azelaic acid and the like. In addition to being useful with polyesters derived from the more common diols and dicarboxylic acids, the brominated diol may be used as a reactive intermediate with other reactants including glycerol, sorbitol, pentaerythritol, methoxypolyethylene glycol, neopentyl glycol, monohydroxypivalate, trimethylolpropane, trimesic acid, p,p'-dicarboxydiphenylmethane, p,p'dicarboxydiphenoxyethane, p-carboxyphenoxyacetic acid and the like.

As appreciated in the art, the dibasic acids mentioned above such as adipic acid, azelaic acid or dimer acids are generally used to improve the dyeability of the polyester. Sulfonated isophthalic acid may also be employed for this purpose. In general, the amounts of these reactants should not exceed about 3 mole percent of the polyester.

The copolymer esters of this invention, i.e., those which are formed from a mixture of brominated diol of the type described above and a conventional glycol, are preferably made by incorporating in the reaction mixture either ethylene glycol or 1,4-cyclohexanedimethanol as the other glycol. Preferably, such mixtures are reacted with terephthalic acid and dimethyl terephthalate; the latter being utilized in a well-known type of ester interchange reaction.

As appreciated in the art, the molecular weight of the polyester must be sufficient to form a suitable fiber if that is the intended purpose of the polyester. Thus, it is preferred to prepare polyesters of the type described above having a number average molecular weight in the range of about 10,000 to about 50,000.

Polyesters obtained by the present invention may be treated in accordance with conventional techniques for modification and further treatment of the polyester fibers. Thus, the copolymers of this invention can be compounded with known stabilizers, lubricants, plasticizers, dyes, antistatic agents and the like. The blending may be conducted by conventional techniques such as by incorporating the adjuvants or additive materials in the mixture to be polymerized or by blending, typically melt blending, after the polymer is made.

Fibers and filaments of the present invention are prepared by conventional procedures such as melt extrusion and by spinning from solution. Cold drawing can be utilized to orient the fibers. Such fibers may be used to prepare monofilaments, yarns, tows, or cords. These may be readily knitted or woven. They can be used in textile applications alone or can be blended with other materials such as cotton, rayon or other polyester. Of the blended fabrics, cotton/polyester blends are preferred. As is well known, polyester fibers are useful in clothing, draperies, and carpeting. The polyesters of this invention can be used in those applications.

The fire retardant properties of the polyesters of this invention can be measured by conventional procedures such as the Limiting Oxygen Index or by a vertical flame test. Usually, the amount of fire retardance is directly proportional to the amount of brominated diol. In general, best flame retardancy is achieved when the bromine content of the polyester is at least about 7 weight percent.

Thus, in a broad aspect this invention provides $\alpha,\alpha'$-bis(hydroxyalkoxy) xylenes which can be made by reacting a glycol with an $\alpha,\alpha'$-dibrominated xylene, preferably having a plurality of halogen atoms, more preferably bromine atoms substituted on the xylene ring. The starting materials have the general formula

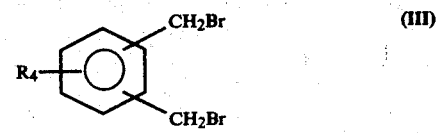

wherein R is selected from —H, —Cl, and —Br, preferably —H and —Br, most preferably such that from 2 to 4 of the radicals indicated by R are bromine, and any other R radicals are —H. For better efficacious results, the reaction is conducted in the presence of two moles of an alkali metal carbonate such as $Na_2CO_3$ or $K_2CO_3$.

Preferred compounds of this invention can be depicted by

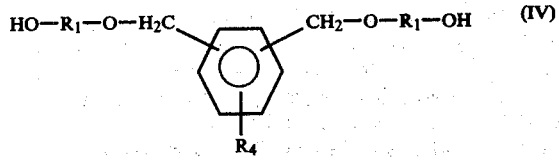

wherein R is as described above and $R_1$ is an aliphatic radical preferably of 2-10 and more preferably 2—4 carbons. More preferred compounds have the formula

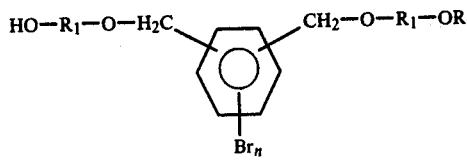 (V)
wherein $R_1$ is from 2 to 4 carbons and n is 2 or 4; more preferably n is 4.
Also provided is the use of these compounds as chemical intermediates and as fire retardants.
In a preferred aspect, linear polyesters made from such compounds are also provided; as described above.
We claim:
1. α,α'-bis(2-hydroxyethoxy)-2,3,5,6-tetrabromo-p-xylene.
* * * * *